United States Patent [19]
Bell

[11] Patent Number: 5,817,103
[45] Date of Patent: Oct. 6, 1998

[54] UMBILICAL CORD COMBINED DISINFECTANT, CLAMP, CUTTER AND CONTAINMENT SYSTEM

[76] Inventor: Lorraine Bell, 196 Bouchelle Rd., Northeast, Md. 21901

[21] Appl. No.: 911,660

[22] Filed: Aug. 15, 1997

[51] Int. Cl.⁶ .......................... A61B 17/42; A61B 17/08; A61B 17/32
[52] U.S. Cl. ..................... 606/120; 606/151; 606/167
[58] Field of Search .............................. 606/1, 120, 151, 606/157, 205

[56] References Cited

U.S. PATENT DOCUMENTS

| | | |
|---|---|---|
| 1,710,766 | 12/1929 | Dilworth . |
| 3,106,919 | 10/1963 | Churchville . |
| 3,323,208 | 6/1967 | Hurley, Jr. . |
| 4,026,294 | 5/1977 | Matler . |
| 4,716,886 | 1/1988 | Schulman et al. . |
| 4,781,188 | 11/1988 | Collins . |
| 5,415,665 | 5/1995 | Hessel et al. ............................ 606/120 |
| 5,676,672 | 10/1997 | Watson et al. ........................... 606/120 |

Primary Examiner—Glenn K. Dawson
Attorney, Agent, or Firm—C. Emmett Pugh; Pugh/Associates

[57] ABSTRACT

An obstetrical combined disinfectant, clamp, cutter and containment system for umbilical cords, being housed in a comprehensive unit and having increased efficiency in the area of motion saving and exposure to infectious organisms during the birthing process and when exposure to infectious organisms is undesirable. A housing contains three umbilical clamps as part of the overall housing of the unit and two pair of serrated, cutting blades incorporated into the housing by way of bonding to the housing structure of the unit. After the baby's umbilical cord is placed horizontally in the unit, the disinfectant makes contact with the cutting sites of the umbilical cord, followed by the closing of the unit, simultaneously clamping and cutting the cord, whereafter the unit is twisted at the perforated midpoint, separating the fetal umbilical stump from the maternal end of the umbilical cord. Following separation, both maternal and infant cord ends remain in a clean environment, being totally enclosed in individual compartments. The maternal portion of the device is easily discarded after expulsion of the placenta. The infant's unit will remain in place from five to seven (5–7) days, at which point the cord gradually atrophies and the unit falls off.

12 Claims, 5 Drawing Sheets

UMBILICAL CORD COMBINED DISINFECTANT, CLAMP, CUTTER AND CONTAINMENT SYSTEM

TECHNICAL FIELD

The present invention relates to an umbilical cord combined disinfectant, clamp, cutter and containment device for, for example, the reduction of infection in hospitals, developing areas and disaster and refugee situations, and more particularly to an obstetrical disinfecter, clamp, cutter and containment system for umbilical cords, using a device housing disinfectant, umbilical clamps and cutters that is able to be broken apart with the infant's side left in place on the umbilical cord until the cord atrophies and it and the device fall off from the infant.

BACKGROUND ART

A baby's umbilical cord is a tubular structure, containing two arteries and one vein which connect the fetus to the maternal placenta. While in utero, the cord serves as a medium for the exchange of waste products and oxygen and nutrients between the mother and her fetus. In delivery of a newborn infant, once the fetus has traversed the birthing (vaginal) canal, it is necessary to separate the infant from the maternal placenta by cutting the umbilical cord and interrupt the loss of blood, which would otherwise occur, by means of clamps. At birth, the method for severing the umbilical cord involves the use of tying devices to clamp the cord for the stoppage of blood flow and a type of sharp blade to sever the cord between the two clamped points.

In developing areas and disaster and refugee situations where health care infrastructure and water are scarce or non-existent, most women deliver their infants with the help of family or traditional birth attendants on dirt floors, unsanitary mats or in the fields. The traditional method for severing the umbilical cord is to use string or bamboo to clamp the cord and a severing type implement, often contaminated, to cut the cord.

Following birth, according to some cultures, the umbilical cord is coated with various substances, such as cow dung or clarified butter ghee, which may be contaminated with bacterial and viral contaminants, especially the *Clostridium Tetani* organism. With such unsanitary conditions, there exists a much higher rate of infant and maternal mortality due to infectious processes, such as bacterial infections and neonatal tetanus, taking the lives of one-half million (500,000) infants worldwide in the first few days of life.

There has been an effort by development agencies and disaster agencies to provide birthing kits, but these typically involve several items, many which can be contaminated, lost or undesirably reused in another delivery process.

In contrast the present invention provides an easily used and beneficial device to simultaneously disinfect the umbilical cord at the area where it is severed, clamp and cut the cord. In addition, the device of the invention maintains a clean environment by allowing the device to then be separated into two parts, leaving the device in place on the infant, thereby protectively containing the cut cord portion for a desirable period of time, eliminating access to the umbilical stump wound where organisms can enter, until the cut cord portion atrophies and falls off.

A list of prior patents having to do with some prior umbilical cord devices, which may be of interest, is provided below:

| Pat. No. | Inventor | Issue Date |
|---|---|---|
| 1,710,766 | Dilworth | 12/27 |
| 3,106,919 | Churchville | 10/63 |
| 3,323,208 | Hurley, Jr. | 6/67 |
| 4,026,294 | Matler | 5/31/77 |
| 4,716,886 | Schulman et al | 01/05/88 |
| 4,781,188 | Collins | 11/01/88 |

However, each of these devices suffer from the disadvantage of failing to contain a non-reusable, comprehensive disinfecting, and a clamping and cutting system that reduces the incidence of bacteria entering the umbilical cord and causing infection. In addition, some of the above devices have several parts, which can be dislodged and render the umbilical cord device unusable.

Thus, an object of the present invention is to provide a device which is able to simultaneously disinfect, clamp and sever the umbilical cord within a clean environment, and following, to twist the device and separate the fetal and maternal ends of the umbilical cord while leaving them in a bacteria protected environment.

Another object of the present invention is to provide a comprehensive unit with clamps built in to the housing of the preferably non-metallic unit, which is inexpensive to produce, thereby permitting the device, for example, to be provided at low cost for developing areas and in disaster and refugee situations.

A further, added feature of the present invention is the protection of health care personnel. When the umbilical device of the present invention is utilized, there will be a reduction in the amount of blood fluid spurt at the time of cord severance, thus decreasing occupational exposure to persons assisting with the birth.

GENERAL SUMMARY DISCUSSION OF INVENTION

In accordance with the present invention, these and other objectives are achieved in the following manner. The present invention's housing is comprised preferably of non-metallic material and includes a comprehensive, combined system for the disinfection, clamping and severing of the umbilical cord in a single step, with part of the device being protectively left on the infant's part of the severed cord for a desirable but relatively short period of time.

The device preferably is rectangular in shape in longitudinal cross-section and has rounded corners, shaped, for example, somewhat like a cylindrical barrel and being of the exemplary dimensions of exactly or at least about two inches by three and a half (2"×3.5") in longitudinal cross-section in width and length, respectively, with an exemplary diameter of about one (1") inch. In the mid-portion of the housing of the unit, there preferably is a perforated line or other weakened area, which, when twisted, allows the easy separation of the two end halves of the unit from one another, including one end half to be protectively left on the infant for a limited period of time.

The exemplary embodiment's preferred triple clamping device employs at least two clamps in close proximity to each other, preferably with an additional, intermediate clamp to ensure stoppage of blood on the fetal end of the umbilical cord, each clamp being part of the overall housing of the preferably non-metallic unit. The device is connected along one side by a hinge portion for allowing one side half to be pivotally moved toward the other side half, along with a latching device located at the other, opposed side for keeping the clamped side halves in a closed position. The clamps preferably are identical to each other, preferably having one or more serrated teeth to ensure maximum compression of the cord and secure locking of the unit's side halves when closed. Once latchingly closed, the clamps preferably cannot be reopened, which, of course, facilitates the continuance of a clean, protective environment over the cut portion of the cord.

The embodiment's exemplary four cutting blades of the device preferably are located adjacent to the middle partitions of the device and the clamps closest in proximity to one another. The preferably metallic cutting blades are attached to the housing of the unit, preferably two on the top side portion of the unit and two on the bottom side portion of the unit, preferably being molded into the housing of the unit, preferably forming an integrated unit with no loose parts.

Overlaying the middle clamps and cutting blades is preferably a thin plastic membrane containing a liquid disinfectant solution, for example, seventy (70%) percent isopropyl alcohol. This acts as a disinfectant and comes in contact with the umbilical cord, bursting the membrane and bathing the umbilical cord with the disinfectant preferably before the cord is severed.

As now should be understood, a primary advantage of the present invention over other devices is it's ability to disinfect, clamp and cut the umbilical cord in a clean environment, in one quick and easy step, while then allowing the fetal and maternal ends of the cord to be separated while maintaining a clean environment for at least the infant's side of the cord cut portion until the umbilical stump atrophies and falls off.

BRIEF DESCRIPTION OF DRAWINGS

For a further understanding of the nature and objects of the present invention, reference should be had to the following detailed description, taken in conjunction with the accompanying drawings, in which like elements are given the same or analogous reference numbers, and wherein:

FIG. 1 is a perspective view of an initial, exemplary embodiment of the umbilical device of the present invention, shown in its fully open disposition; while FIGS. 3 and 4 are cross-section views of the exemplary umbilical device of FIG. 1, taken along section lines 3—3 and 4—4, respectively; while

EXEMPLARY MODES FOR CARRYING OUT THE INVENTION

FIGS. 1–7 illustrate the initial, exemplary, preferred embodiment of the apparatus of the present invention of the fully contained, preferably non-metallic housing which preferably contains the basic housing and clamps molded as one, single unit. The initial, exemplary umbilical device of the present invention will be illustrated by the number 10 with the umbilical cord generally designated "UC."

Figure 1:
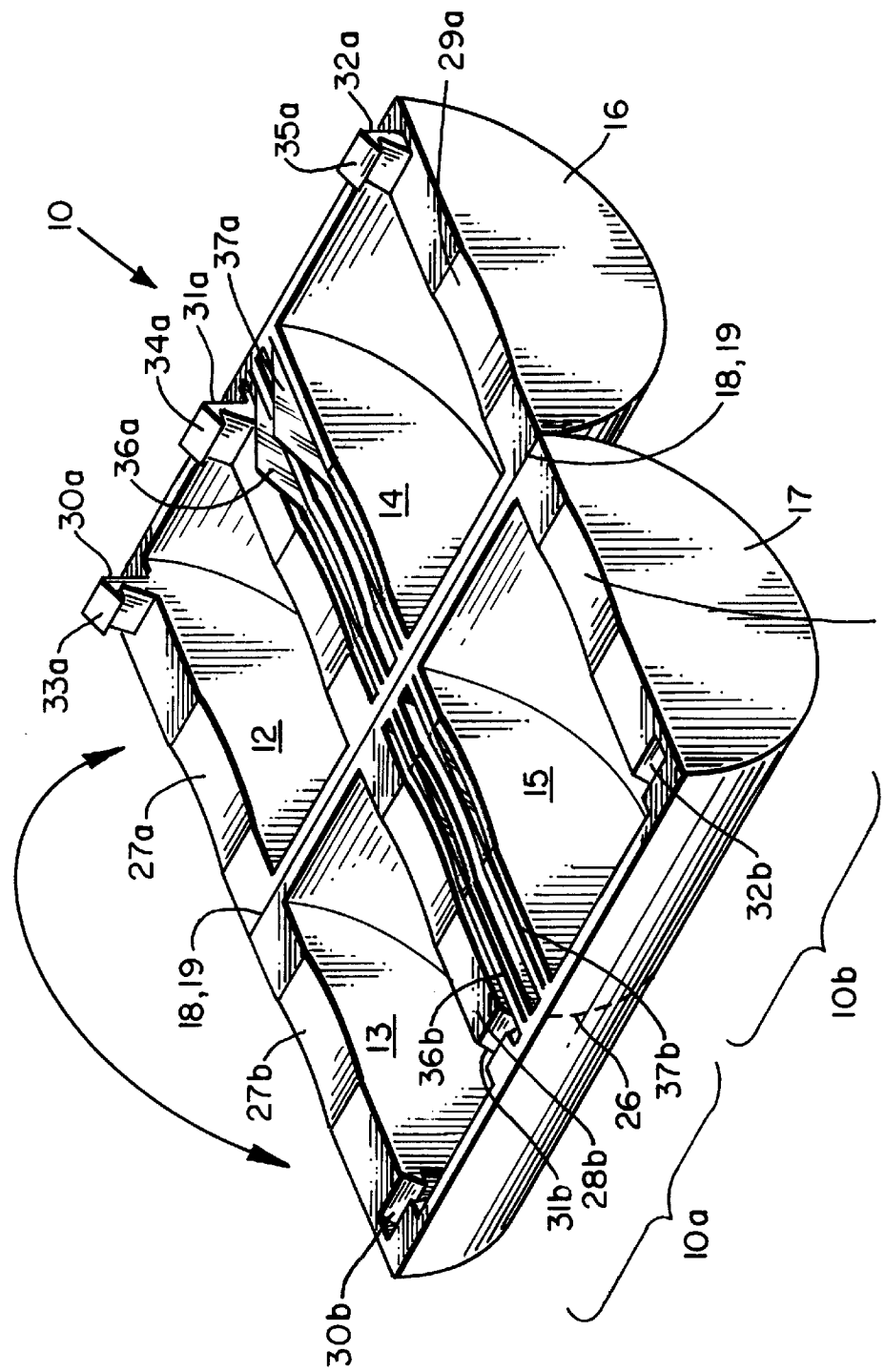
Figure 2:
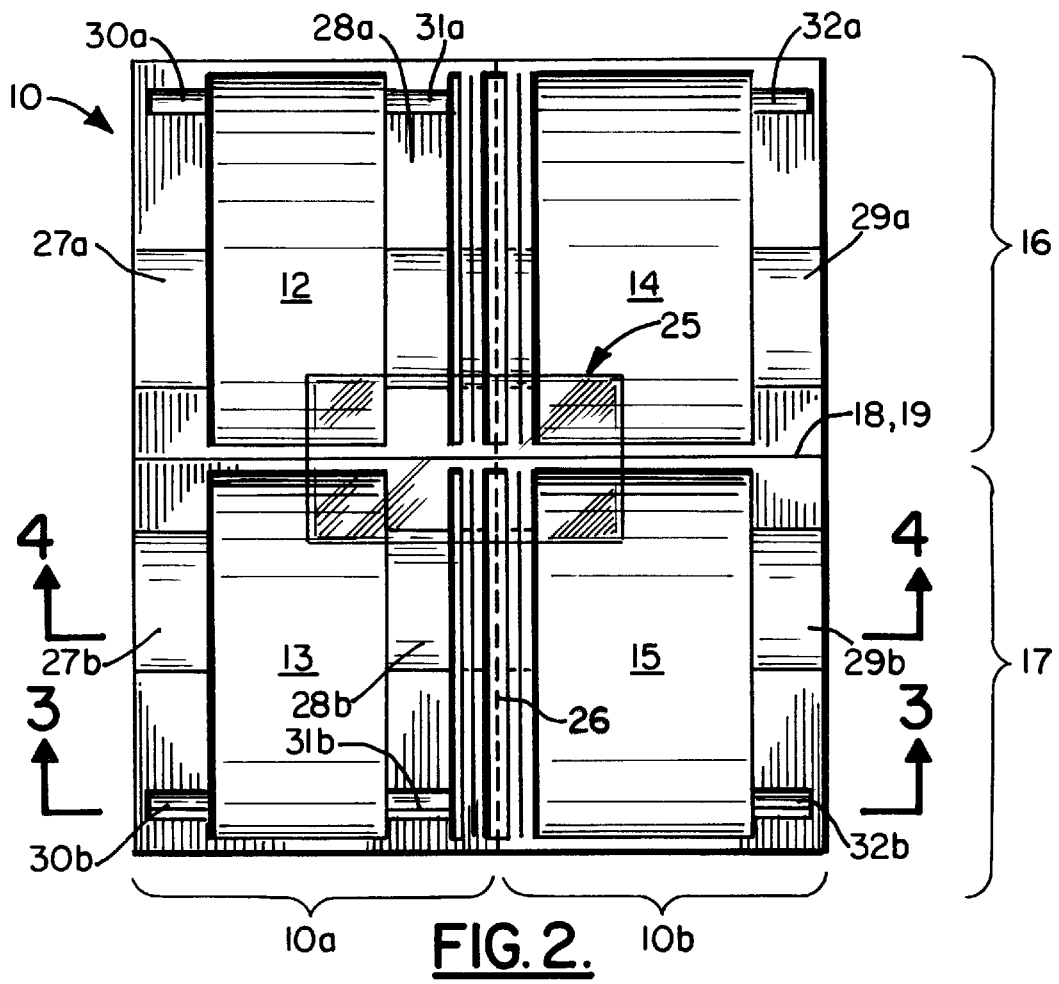
FIG. 2 is a plan view of the exemplary umbilical device of FIG. 1, likewise in its fully open disposition.
Figure 3:
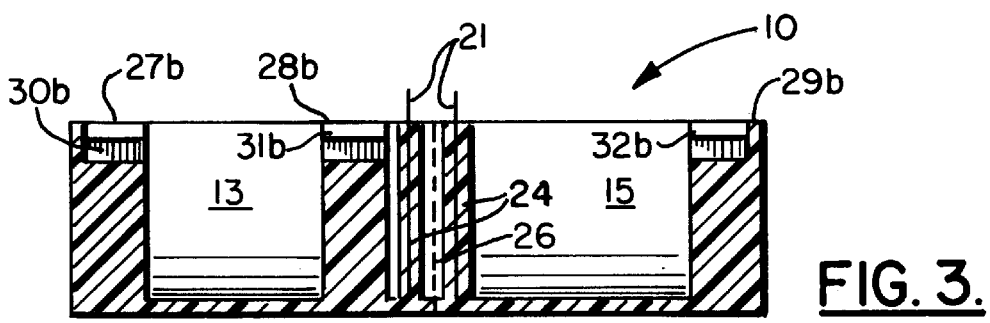
Figure 4:
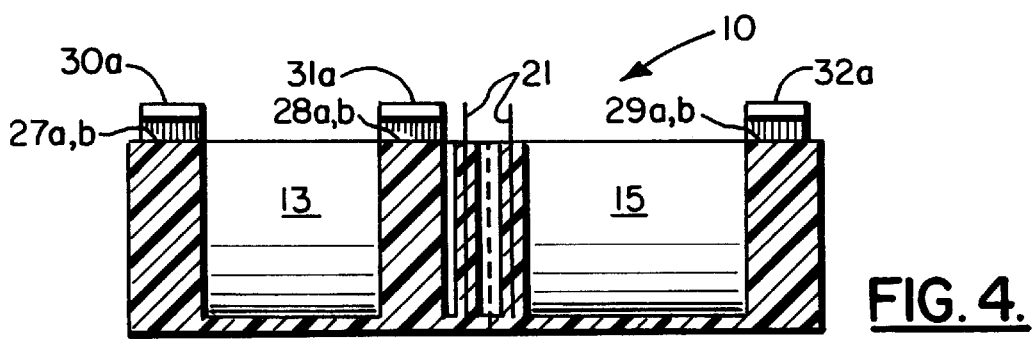
Figure 7:
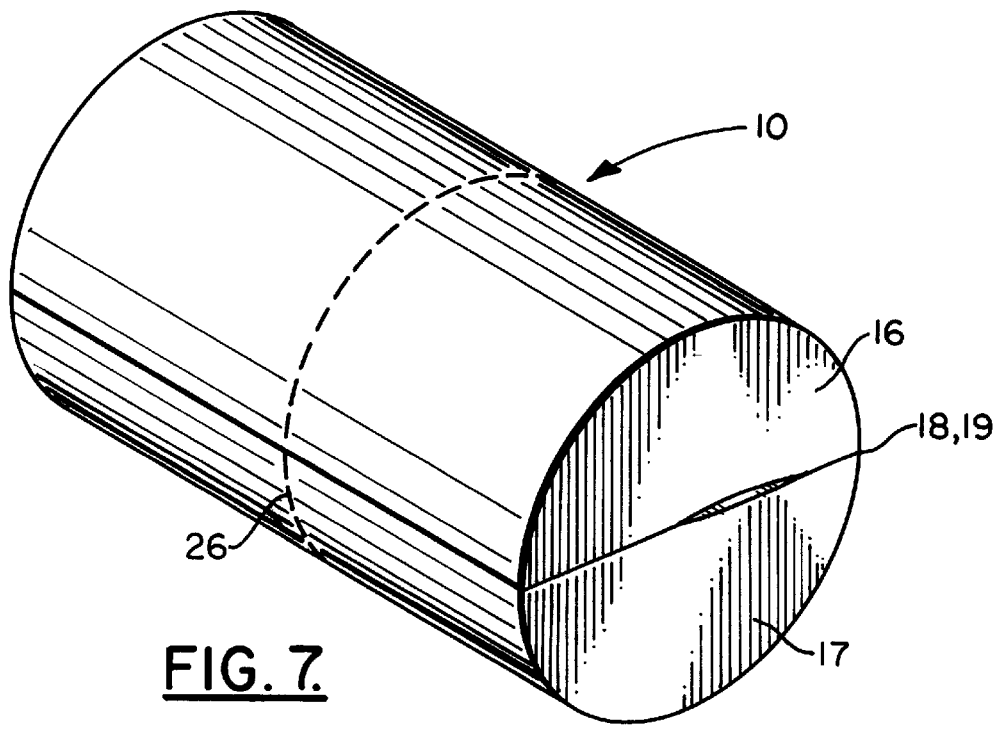

In FIG. 1 is the illustration of the composite apparatus 10, having rounded edges and an overall cylindrical, barrel-like shape (when closed; see FIG. 7), including an upper (16) and lower (17) half, side portions, made preferably of a non-metallic molded material, such as, for example molded plastic. The movement of and general structure of the upper, half, side portion 16 of the unit 10 and the lower, half, side portion (17) of the unit 10 are similar in shape and size and pivotally moveable relative to one another (note curved direction arrow) between a fully open disposition, as seen in FIGS. 1 & 2, and a fully closed disposition, as seen in FIG. 7. The movement of the top portion 16 to the bottom portion 17 in relation to one another is accomplished by an effective hinge piece or portion 18/19 preferably integrally molded as part of the non-metallic housing joined to the back edge 18 of the top half 16 (FIG. 1) and the back edge 19 of the bottom half portion 17, so that the top portion 16 and bottom portion 17 will be forcibly closed over and around the umbilical cord to attain a closed position when in use.

In FIGS. 1 and 2, located at the mid-portion of the outer aspect of the housing is a perforated line or weakened area 26, which, when the interior fetal 12, 13 and maternal 14, 15 portions of the device 10 are twisted with respect to one another, will cause the unit to separate into two sub-units 10A & 10B. As seen in FIG. 2, each unit has partitions 24 which cover the end of each separable sub-unit 10A & 10B to close them off, particularly the fetal sub-unit 10A, facilitate a clean environment.

Referring particularly to FIG. 2, a thin plastic container 25, formed from a single bag as illustrated (or dual, juxtaposed bags) located in the interior of the unit 10 and overlaying both the fetal and material interior portions 12/13, 14/15, respectively, contains a liquid disinfectant solution, such as, for example, seventy (70%) percent isopropyl alcohol, which is attached to the back hinge of the unit 10 to ensure correct placement near the portion of the umbilical cord that is to be severed. When the umbilical cord is placed horizontally inside the unit 10 on top of the disinfectant container 25 and compressed when closing the top 16 and bottom 17 portions of the unit 10 together, the container 25 of isopropyl alcohol will burst, bathing the umbilical cord and effectively disinfecting the area to be severed. (For simplicity sake, the disinfectant container 25 shown in FIG. 2 is not shown in the other figures.)

As can be seen, inter alia, in FIGS. 1 and 2, three, parallel sets of opposed, umbilical clamping surfaces 27A/27B, 28A/28B, 29A/29B are substantially identical to each other, except for their relatively positions as integral parts of the unit 10. Located at the opposed ends of the clamping surfaces are inter-mating, locking latching members 30A/30B, 31A/31B, 32A/32B, the upper side including latching teeth 33A, 34A & 35A and the lower side including mating, latching openings 30B, 31B & 32B, with the clamping surfaces 27A/27B, 28A/28B and the locking latching members 30A/30B, 31A/31B being on the fetal end sub-unit 10A and the opposed clamping surfaces 29A/29B and latching members 32A/32B being on the maternal end sub-unit 10B. The upper, latching arms 30A, 31A & 32A serve as male members which are inserted and lock into the mating female openings 30B, 31B & 32B, respectively, securely locking the upper and lower side halves 16 & 17 together when the halves are closed together into the fully closed position illustrated in FIG. 7. The clamp interlocking arms & openings or slots 30A/30B, 31A/31B, 32A/32B, when locked together, cannot be reopened, facilitating the maintaining of a clean environment with less exposure to pathogenic organisms.

Figure 5:
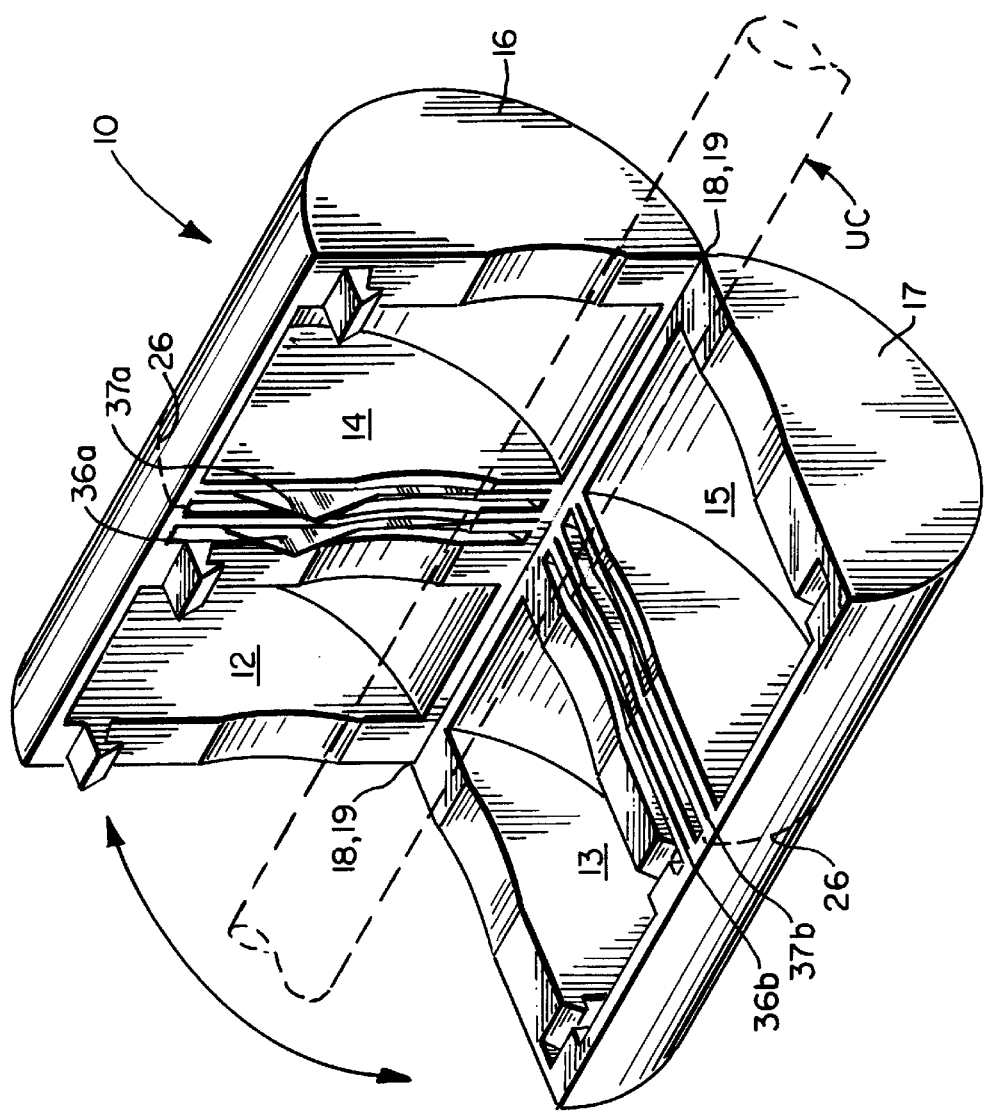
FIGS. 5, 6 and 7 are perspective views of the exemplary umbilical device of FIG. 1, but shown in its half-open/half-closed, three-quarters, and fully closed dispositions, respectively.
Figure 6:
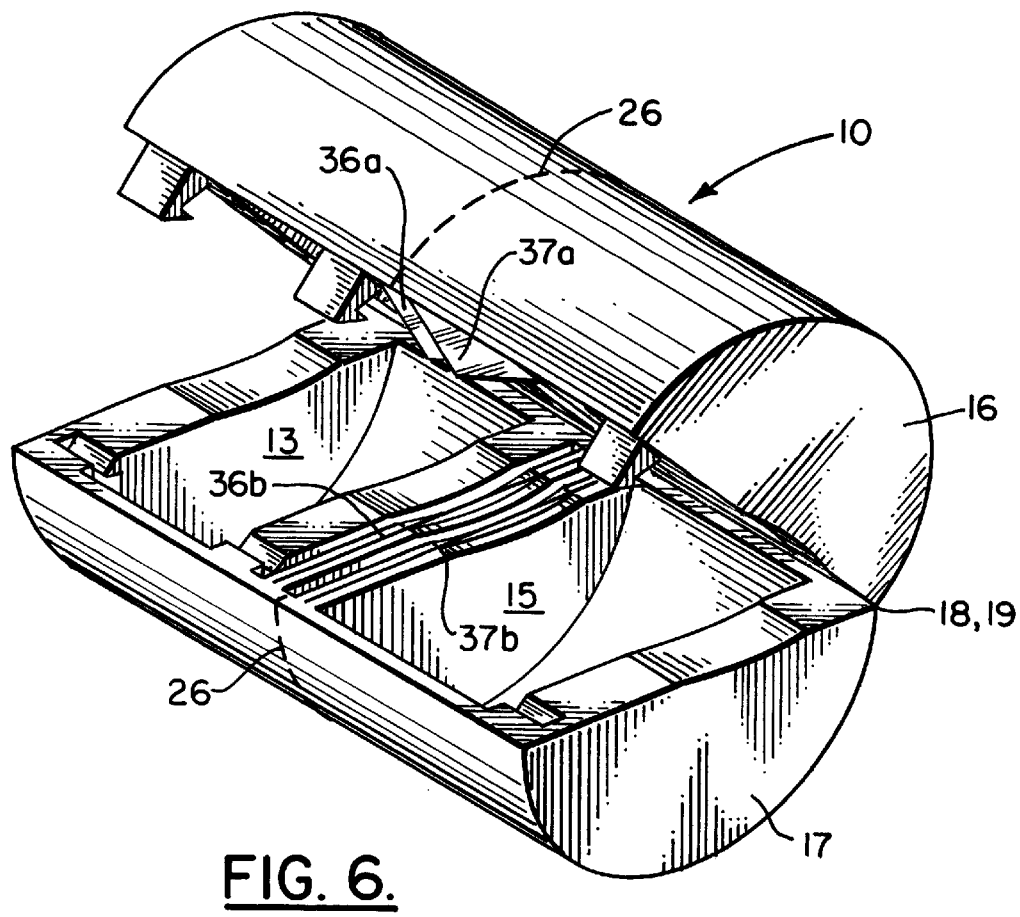

Reference is now made to FIGS. 1, 5 & 6, illustrating the cutting mechanism or device of the unit 10, in which there are an exemplary two pair 21 of opposed blades 36A/36B, 37A/37B, for a total of four (4) blades, made preferably of metallic material and bonded into the housing of the unit 10. One set of opposed blades 36A/36B is located adjacent to the opposed clamping surfaces 28A/28B on the fetal side 10A of the unit 10, and the other set 37A/37B is located adjacent to the weakened, perforated line 26 located in the mid-portion area of the housing, on the opposite side of the line 26 from the first set of blades, on the maternal side 10B of the unit 10.

Internal partitions 24 ultimately serve as the outer end wall surfaces for the sub-units 10A & 10B, when they are separated from one another. When so separated, the fetal sub-unit 10A preferably will have its own opposed, end portions, each having an associated clamping surface, while the maternal sub-unit 10B will have one clamping surface located at its end portion distal to the fetal sub-unit.

An alternative, further exemplary embodiment for the cutting mechanism or device is the use of one or more strands of associated cutting wire extending laterally across the housing in its mid-portion area in place of the laterally extending cutting blades, or as a further alternative using a single blade or wire working against an appropriate cutting surface, comparable to cutting against a cutting board surface. The housing is preferably cylindrical, as illustrated, or could be configured in an oval shape or box-like shape or some other appropriate, shape, preferably longitudinally extended and rounded.

Exemplary dimension for the unit 10 are a longitudinal width of, for example, about three and a half (3.5") inches or about four (4") inches, and a width, for example, of about two (2") inches closed or four (4") inches open. An exemplary diameter is equal to or about one (1") inches and fits comfortably in the human hand for easy manipulation and operation of the device. The exemplary widths of the opposed clamping surfaces 27A/27B, 28A/28B & 29A/29B are, for example, about a quarter to about three-eighths (¼" to ⅜") inches.

When in use, the housing of the unit 10, with its upper and lower side, halves 16 & 17, is closed around the umbilical cord "UC," which is placed across the longitudinal length of the unit preferably over or under the disinfectant bag 25 or in an intermediate area in the area where the tips of the upper blades 36A & 37A will pass, and, as the closing is taking place, the opposed sets of blades 36A/36B, 37A/37B move with respect to their opposed mates in a scissor-like motion to sever the umbilical cord "UC" from the superior and inferior aspects, effectively cutting and severing the umbilical cord.

Thereafter, the two sub-unit portions 10A & 10B are twisted apart at the weaken, perforation line 26, and separated from one another, producing the fetal sub-unit 10A and the separated maternal sub-unit 10B, with the former being left with the infant until the severed cord portion atrophies and falls off, with the fetal sub-unit. The latter (10B) is disposed of with the maternal after-birth material.

Figure 8:
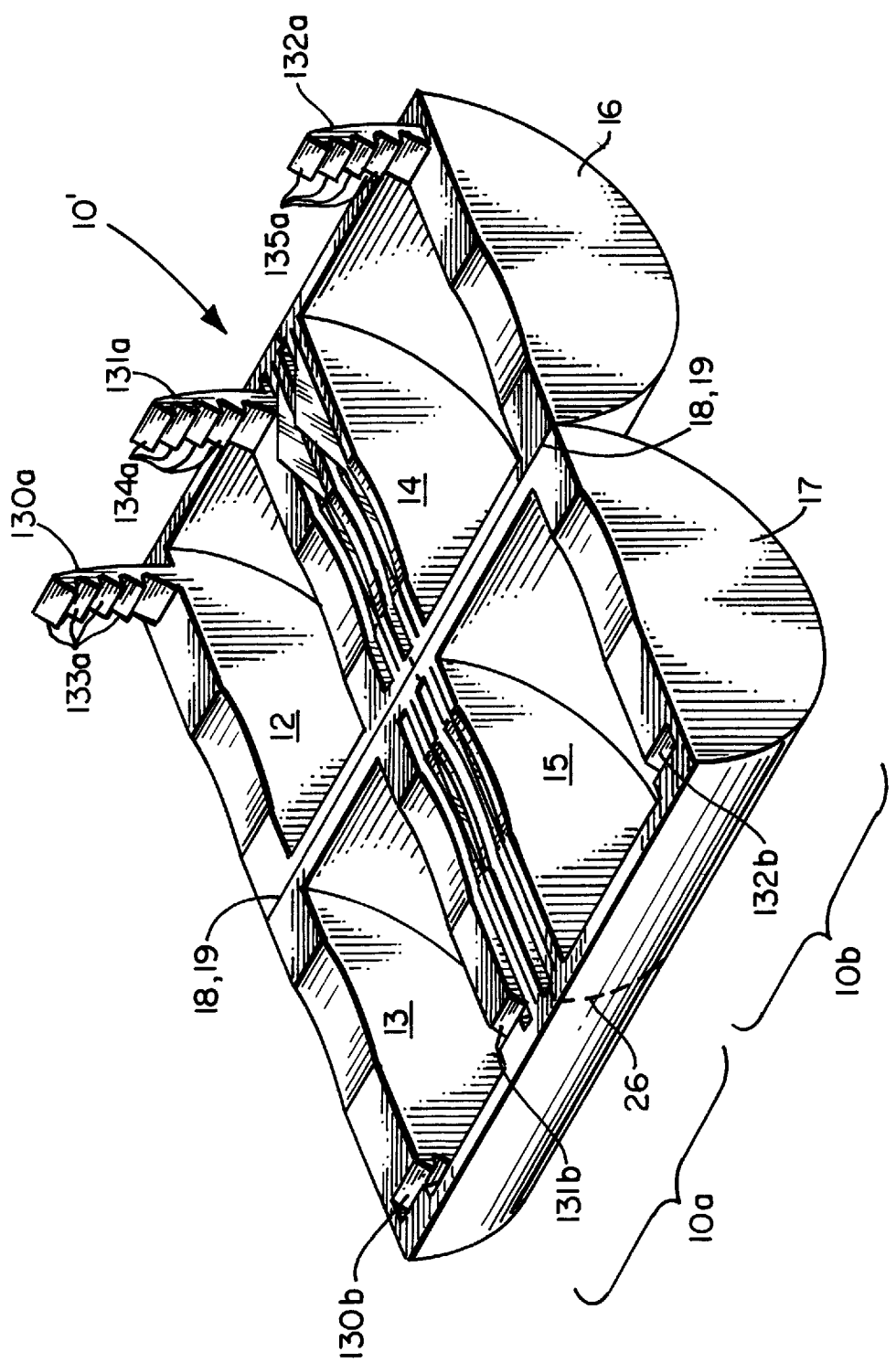
FIG. 8 is a perspective view, similar to that of FIG. 1, but of second, alternative, exemplary embodiment in which more serrated teeth are included on the clamping arms for greater security in keeping the device closed after it has been applied to the umbilical cord, particularly on the infant's portion of the severed cord.

An exemplary alternative embodiment of the umbilical cord combined device 10' is illustrated in FIG. 8 and is substantially the same as the initial embodiment 10, except that the clamping or locking, male arms 130A, 131A & 132A have multiple "teeth" or ridge projections 133A, 134A & 135A, respectively, which mate with a like number of like configured ridges or indentations contained within the mating female openings 130B, 131B & 132B, in similar fashion to the arms and openings of unit 10. This provides a more secure latch and locking mechanism for the two side halves 16 & 17 when they are closed and latched together (as analogously shown in FIG. 7). Because the rest of the structure and the methodology are the same for the embodiments 10 & 10', the structure and methodology of use for the unit 10' will not be further discussed for brevity's sake.

Thus, an exemplary embodiment of the present invention preferably includes:

preferably a non-metallic umbilical-cord/combined-disinfecter-clamp-and-cutting apparatus as one, integrated unit, preferably comprising:

a. a base member or housing 10 (10') having upper and lower, side-half portions 16 & 17, the upper and lower portions being joined by a back hinge piece or portion 18/19 preferably made of the same non-metallic material, enabling the opposed, side-halves to be positioned initially in an open or subsequently closed dispositions (FIG. 1 vs. FIG. 7) in relation to each other;

b. clamping & associated locking means within the upper and lower portions of the device, including preferably at least three sets of parallel, longitudinally spaced, laterally extended, umbilical clamping surfaces 27A/27B, 28A/28B & 29A/29B as preferably an integral part of the housing of the unit, each set of clamping surfaces having associated therewith a set of an opposed, male arms 30A, 31A & 32A (130A, 131A & 132A) and matable female openings 30B, 31B & 32B (130B, 131B & 132B) at their opposed edges away from the hinge edge 18/19, the arms and opening becoming lockingly engaged and latched together when the unit is fully closed, with the clasp or latching mechanism preferably being unable to be re-opened once latchingly closed; there further preferably be included serrations or roughened areas on the opposed clamping surfaces to enhance the maximum gripping of the umbilical cord upon closure;

c. an exemplary two pairs of opposed cutting blades 36A/36B, 37A/37B positioned in close proximity to the two medial partitions, located on the upper and lower portions of the unit, so that, when the unit is closed, each pair is approaching and moving in a scissor-like fashion, causing the umbilical cord to be severed from the superior and inferior aspects and ensuring complete severance of the cord; and d. a plastic bag 25, or other appropriate container(s), containing preferably a liquid disinfectant solution of, for example, seventy (70%) percent isopropyl alcohol, preferably horizontally overlays the mid-portion area of the device, covering both the fetal and maternal aspects of the device or otherwise positioned to be opened or broken to dispense the disinfectant in association with the closing of the unit and the cord severance; the container of disinfectant being enclosed within at least one, preferably thin plastic film bag which cushions the umbilical cord, and bursts upon pressure when the unit is closed, exposing the umbilical cord to the seventy (70%) percent isopropyl alcohol disinfectant preferably before cord clamping and cutting take place; the cutting blades passing through the thin plastic wrapping of the isopropyl alcohol preferably before the umbilical cord is severed, effectively disinfecting the cord area.

Additionally, as part of the housing of the invention, there preferably is included:

e. a perforated line or other weakened area encompassing preferably the entire mid-point of the device, allowing easy separation of the fetal and maternal parts of the device by, for example, twisting the two sub-units in opposite directions.

After the unit 10 has been fully closed around the umbilical cord UC, appropriate movement, for example, opposed twisting of the housing at the weakened, perforated line 26, allows the device to be separated into the two individual sub-units 10A & 10B, each sub-unit being within itself a closed and locked sub-unit, one sub-unit 10B housing the maternal end of the umbilical cord and the other sub-unit 10A housing the fetal end of the umbilical cord. The fetal sub-unit 10A is left in place until the umbilical stump atrophies and falls off, providing protection to the infant during this limited waiting time period.

The basic method of application thus involves:

(1) initially inserting the unit 10 about the umbilical cord "UC;"

(2) moving the two side halves 16 & 17 of the unit 10 together toward the unit's closing disposition, thereby simultaneous or sequentially bursting the disinfectant solution container, disinfecting the umbilical cord, and severing the cord in a disinfected environment;

(3) locking the two halves together as the two halves are fully closed together;

(4) thereafter separating the unit into two, fetal & maternal sub-units 10A & 10B, respectively, by, for example, twisting the sub-unit portions about a weakened area, and, after separation of the two sub-units; and (5) allowing the fetal sub-unit 10A to remain on the infant's portion of the umbilical cord until the severed cord atrophies and the fetal sub-unit falls off or is otherwise affirmatively removed when otherwise desired.

It is noted that the embodiments described herein in detail for exemplary purposes are of course subject to many different variations in structure, design, application and methodology. Because many varying and different embodiments may be made within the scope of the inventive concept(s) herein taught, and because many modifications may be made in the embodiments herein detailed in accordance with the descriptive requirements of the law, it is to be understood that the details herein are to be interpreted as illustrative and not in a limiting sense.

What is claimed as invention is:

1. An umbilical-cord/combined-disinfecter-clamp-and-cutting device, combined as one unit, comprising:

a. a longitudinally extended housing having upper and lower portions forming opposite sides, said upper and lower portions being joined by a hinge-like member about which said upper and lower portions can pivot, enabling the opposite sides to be positioned in an open, separated disposition and, alternatively, a closed disposition, in relation to each other;

b. at least two, longitudinally spaced, clamping surfaces within said upper and lower portions contained as an integral part of said housing, and at least one latch engageable to hold said upper and lower portions together when they are in their closed disposition;

c. at least one cutting device positioned on one of said opposite sides and extendible past said one of said opposite sides and being extendable into the other opposite side so that, when said upper and lower portions are in their closed disposition, said cutting device causing the umbilical cord when positioned between said upper and lower portions to be severed; and d. a container portion containing a liquid disinfectant attached to said housing and positioned adjacent to said cutting device, said container portion being opened when said upper and lower portions are in their closed disposition by the action of moving said upper and lower portions together, effectively dispensing said disinfectant, disinfecting the area where the umbilical cord is severed.

2. The umbilical cord device of claim 1, wherein said container portion comprises:

at least one plastic bag.

3. The umbilical cord device of claim 1, wherein said liquid disinfectant comprises:

about seventy (70%) isopropyl alcohol.

4. The umbilical cord device of claim 1, wherein said housing includes a mid-area portion, and wherein said housing further includes:

a weakened area located circumferentially around the mid-area portion of said housing; the forcing of the housing in opposite directions on opposite sides of said weakened area causing the housing to be separated into two, individual, separate sub-units, one of which is a fetal sub-unit in which at least at least one of said two clamping surfaces is located, said fetal sub-unit forming a closed enclosure containing at least some of said liquid disinfectant solution and being leaveable on the fetal cord portion of a severed umbilical cord, providing it with a protective environment until the fetal cord portion atrophies and falls off from the infant.

5. The umbilical cord device of claim 4, wherein said fetal sub-unit has opposed end portions, one of which is located at said mid-area portion, and wherein said fetal sub-unit includes:

at least two clamping surfaces, one at either opposed end portions thereof.

6. The umbilical cord device of claim 5, wherein there is further included:

at least three of said longitudinally spaced, clamping surfaces; and wherein the other of said sub-units is a maternal sub-unit having a distal end portion, and wherein said maternal sub-unit further includes:

at least one clamping surface, located at said distal end portion.

7. The umbilical cord device of claim 4, wherein said weakened area comprises:

a perforated line.

8. The umbilical cord device of claim 1, wherein said cutting device comprises:

at least one cutting blade extending laterally across said housing.

9. The umbilical cord device of claim 1, wherein said cutting device comprises:

at least one cutting wire extended laterally across said housing.

10. The umbilical cord device of claim 1, wherein said cutting device further comprises:

a hinge-like member laterally extending along one side edge of said housing, connecting said upper and lower portions together, allowing said upper and lower portions to hingedly pivot with respect to one another to move them from their open disposition to their closed disposition.

11. The umbilical cord device of claim 1, wherein said housing is:

longitudinally extended, rounded and of a size to conveniently fit in the user's hand for easy manipulation and operation of the device.

12. A method of severing an umbilical cord on a new born infant using a device having two, relatively pivotable side-halves, pivotally moveable from an open disposition in which the side-halves have a gap between them, into which the un-severed cord is inserted, and thereafter a closed disposition which severs the cord, with the device including a container of disinfectant solution, comprising the following steps:

(1) initially inserting the device about the umbilical cord;

(2) moving the two side halves of the device together toward the device's closing disposition, thereby simultaneous or sequentially bursting the disinfectant solution container, disinfecting the umbilical cord, and severing the cord in a disinfected environment;

(3) locking the two halves together as the two halves are fully closed together;

(4) thereafter separating the device into two, fetal & maternal sub-units, respectively, by twisting the sub-unit portions about a weakened area, and, after separation of the two sub-units, leaving the fetal sub-unit on the fetal portion of the severed cord; and (5) allowing the fetal sub-unit to remain on the infant's portion of the umbilical cord until the severed cord atrophies and the fetal sub-unit falls off or is otherwise affirmatively removed when otherwise desired.

* * * * *